United States Patent
AlSwisi et al.

(10) Patent No.: US 9,211,335 B2
(45) Date of Patent: Dec. 15, 2015

(54) STABILIZED PHARMACEUTICAL FORMULATIONS COMPRISING ANTINEOPLASTIC COMPOUNDS

(71) Applicant: Hikma Pharmaceuticals, Amman (JO)

(72) Inventors: Mahmoud S. AlSwisi, Amman (JO); Mahmoud A. A. Ghannam, Amman (JO)

(73) Assignee: Hikma Pharmaceuticals (JO)

( * ) Notice: Subject to any disclaimer, the term of this patent is extended or adjusted under 35 U.S.C. 154(b) by 0 days.

(21) Appl. No.: 14/314,405

(22) Filed: Jun. 25, 2014

(65) Prior Publication Data

US 2014/0309197 A1    Oct. 16, 2014

Related U.S. Application Data

(62) Division of application No. 13/826,807, filed on Mar. 14, 2013, now Pat. No. 8,974,811.

(51) Int. Cl.

| | |
|---|---|
| *A61F 2/02* | (2006.01) |
| *A61K 47/02* | (2006.01) |
| *A61L 31/16* | (2006.01) |
| *A61L 27/54* | (2006.01) |
| *A61K 9/00* | (2006.01) |
| *A61K 47/12* | (2006.01) |
| *A61K 9/08* | (2006.01) |
| *A61K 9/19* | (2006.01) |
| *A61K 31/4188* | (2006.01) |
| *A61K 31/495* | (2006.01) |
| *A61K 31/166* | (2006.01) |
| *A61K 31/5395* | (2006.01) |
| *A61K 31/655* | (2006.01) |

(52) U.S. Cl.

CPC ............... *A61K 47/02* (2013.01); *A61K 9/0053* (2013.01); *A61K 9/08* (2013.01); *A61K 9/19* (2013.01); *A61K 31/166* (2013.01); *A61K 31/4188* (2013.01); *A61K 31/495* (2013.01); *A61K 31/5395* (2013.01); *A61K 31/655* (2013.01); *A61K 47/12* (2013.01); *A61L 27/54* (2013.01); *A61L 31/16* (2013.01)

(58) Field of Classification Search

CPC ................................. A61L 31/16; A61L 27/54

See application file for complete search history.

(56) References Cited

U.S. PATENT DOCUMENTS

| | | |
|---|---|---|
| 6,987,108 B2 | 1/2006 | Ugwu et al. |
| 7,786,118 B2 | 8/2010 | Ugwu et al. |
| 2009/0010927 A1 | 1/2009 | Yaffe et al. |
| 2009/0041715 A1 | 2/2009 | Becker et al. |
| 2010/0160208 A1 | 6/2010 | Schlingensiepen et al. |
| 2010/0291222 A1 | 11/2010 | Yu et al. |
| 2012/0283304 A1 | 11/2012 | Pullagurla et al. |

FOREIGN PATENT DOCUMENTS

| | | |
|---|---|---|
| EP | 1 938 798 A1 | 7/2008 |
| WO | WO 99/01118 | 1/1999 |
| WO | WO 03/072082 A1 | 9/2003 |

(Continued)

OTHER PUBLICATIONS

European Search Report mailed Aug. 4, 2014 in European Patent Application No. 14159649.

*Primary Examiner* — Carlos Azpuru

(74) *Attorney, Agent, or Firm* — Merchant & Gould, P.C.

(57) ABSTRACT

The present invention relates to stabilized pharmaceutical formulations prepared from solutions comprising an antineoplastic compound having a cyclic or non-cyclic hydrazine, triazine, or tetrazine group, or a pharmaceutically acceptable salt thereof, and a stabilizer, wherein the stabilizer is an antioxidant and/or more susceptible to nucleophilic attack than the antineoplastic compound.

14 Claims, 1 Drawing Sheet

(56) References Cited

FOREIGN PATENT DOCUMENTS

| WO | WO 2006/060464 A1 | 6/2006 |
| WO | WO 2006/099132 A1 | 9/2006 |
| WO | WO 2008/140724 A1 | 11/2008 |
| WO | WO 2009/127815 A1 | 10/2009 |
| WO | WO 2010/093771 A1 | 8/2010 |
| WO | WO 2011/072218 A2 | 6/2011 |
| WO | WO 2012/028310 | 3/2012 |

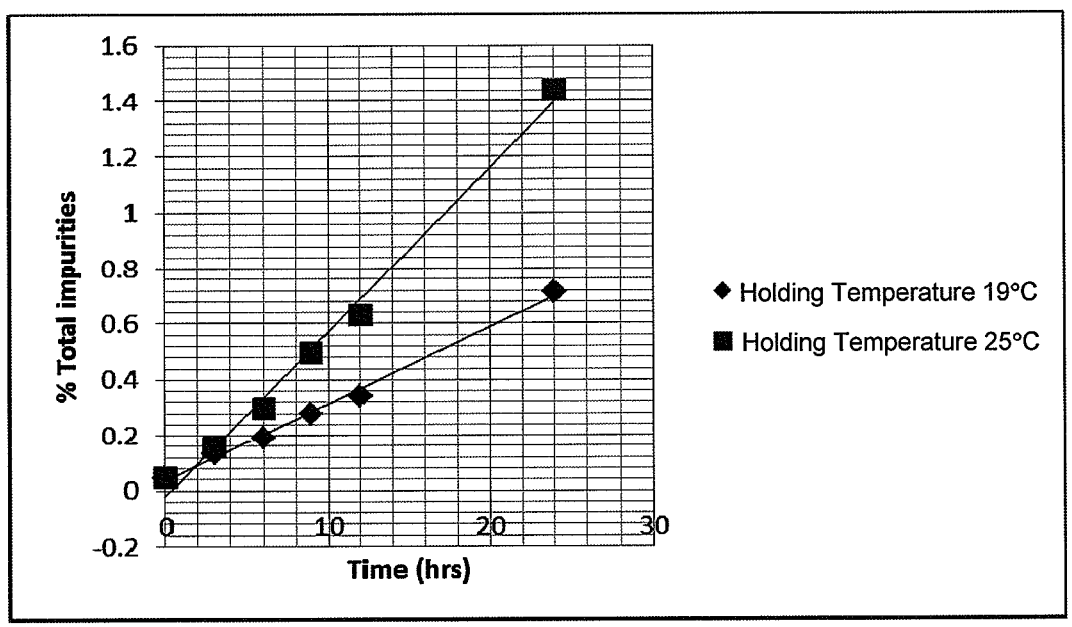

STABILIZED PHARMACEUTICAL FORMULATIONS COMPRISING ANTINEOPLASTIC COMPOUNDS This application is a divisional of U.S. patent application Ser. No. 13/826,807 (now U.S. Pat. No. 8,974,811) filed 14 Mar. 2013, the disclosure of which is hereby incorporated by reference in its entirety.

FIELD OF THE INVENTION

The present invention relates to stabilized pharmaceutical formulations prepared from solutions comprising an antineoplastic compound and a stabilizer.

BACKGROUND

Various compounds having a cyclic or non-cyclic hydrazine, triazine, or tetrazine group are known to have antineoplastic properties. Such compounds include, for example, altretamine, dacarbazine, mitozolomide, procarbazine, temozolomide, and compounds described in U.S. Pat. No. 5,260,291 as having antineoplastic activity. The main degradation reactions for compounds that contain hydrazine, triazine, or tetrazine groups are oxidation and nucleophilic substitution, the latter of which is a well-known reaction in organic chemistry wherein the nucleophile displaces a good leaving group, resulting in an unwanted hydrolysis product.

For example, temozolomide (chemical name: 3,4-dihydro-3-methyl-4-oxoimidazo[5,1-d]-as-tetrazine-8-carboxamide) is a tetrazine derivative known for its anti-tumor effects, and is marketed as TEMODAR®, which is approved for treating adult patients with newly diagnosed glioblastoma multiforme concomitantly with radiotherapy and then as maintenance treatment, and is also approved for treating adult patients with refractory anaplastic astrocytoma—i.e., patients who have experienced disease progression on a drug regimen containing nitrosourea and procarbazine. Temozolomide rapidly hydrolyzes to 5-(3-methyltriazen-1-yl)imidazole-4-carboxamide (MTIC) at neutral and alkaline pH values, with hydrolysis taking place even faster at alkaline pH. TEMODAR® is supplied as a lyophilized powder containing temozolomide, mannitol, L-threonine, polysorbate 80, sodium citrate dihydrate, and hydrochloric acid; and must be kept refrigerated at 2-8° C. until reconstituted. After reconstitution, the product may be kept at 25° C., but only for 14 hours including infusion time.

U.S. Pat. No. 6,987,108 discloses a pharmaceutical formulation comprising temozolomide or a pharmaceutically acceptable salt thereof, at least one aqueous diluent, and at least one dissolution enhancing agent sufficient to substantially dissolve the temozolomide, wherein the dissolution enhancing agent is urea, L-histidine, L-threonine, L-asparagine, L-serine, or L-glutamine. This patent discloses lyophilized formulations of temozolomide which are to be reconstituted with an aqueous diluent before administration. Further, the disclosed formulations require the presence of a dissolution enhancing agent to increase the rate with which temozolomide dissolves.

U.S. Pat. No. 7,786,118 discloses a pharmaceutical formulation comprising temozolomide or a pharmaceutically acceptable salt thereof, at least one aqueous diluent, and L-threonine. The disclosed formulation is reconstituted with an aqueous diluent before administration, and requires the presence of L-threonine as a dissolution enhancing agent that increases the rate with which temozolomide dissolves.

U.S. Patent Application Publication No. 2012/0283304 discloses a temozolomide formulation for parenteral administration that does not require a dissolution enhancing agent and can purportedly be stored below 25° C.

For reasons of product stability, antineoplastic agents are often supplied to clinical practices in lyophilized form. Freeze-dried vials are sometimes stored under refrigerated conditions (e.g., 2-8° C. for TEMODAR®) and reconstituted prior to use.

SUMMARY OF THE INVENTION

The present invention relates to a process for preparing a pharmaceutical formulation, comprising the steps of: (a) dissolving at least one excipient and at least one buffer into an aqueous diluent to form an acidic solution, wherein the temperature of the aqueous diluent is in the range of 16 to 24° C. before addition of the excipient and buffer; (b) dissolving a stabilizer either into the solution of step (a) or into the aqueous diluent of step (a) before addition of the excipient and buffer; and (c) dissolving an antineoplastic compound having a cyclic or non-cyclic hydrazine, triazine, or tetrazine group, or a pharmaceutically acceptable salt thereof, into the solution of step (b) at a temperature in the range of 16 to 24° C.; wherein the stabilizer is an antioxidant and/or more susceptible to nucleophilic attack than the antineoplastic compound.

In at least one embodiment of the present invention, the process further comprises the step of lyophilizing the solution of step (c) to yield a lyophilized powder that contains less than 0.6 wt % of total impurities, based on the total weight of the lyophilized powder, after storage for 3 months at 40° C./75% RH. Preferably, the lyophilized powder contains less than 0.4 wt % of total impurities after storage for 3 months at 40° C./75% RH. Preferably, the lyophilized powder contains less than or equal to 10% of the initial amount of stabilizer added in step (b).

In at least one embodiment of the present invention, the stabilizer is added in an amount of 0.01 to 1% w/v.

In at least one embodiment of the present invention, the process further comprises the step of adjusting the pH of the solution of step (c) to about 3 to about 4.

In at least one embodiment of the present invention, the antineoplastic compound is selected from altretamine, dacarbazine, mitozolomide, procarbazine, and temozolomide. Preferably, the antineoplastic compound is temozolomide.

In at least one embodiment of the present invention, the stabilizer is an antioxidant.

In at least one embodiment of the present invention, the stabilizer is selected from alpha tocopherol, ascorbic acid, ascorbyl palmitate, butylated hydroxyanisole, butylated hydroxytoluene, hypophosphorus acid, monothioglycerol, potassium metabisulfite, propionic acid, propyl gallate, sodium ascorbate, sodium bisulfite, sodium formaldehyde sulfoxylate, sodium metabisulfite, sodium sulfite, and combinations thereof. Preferably, the stabilizer is sodium metabisulfite.

In at least one embodiment of the present invention, the excipient is selected from polysorbate, polyethylene glycol, propylene glycol, polypropylene glycol, and combinations thereof.

In at least one embodiment of the present invention, the buffer is selected from sodium citrate dihydrate, hydrochloric acid, and combinations thereof.

In at least one embodiment of the present invention, the aqueous diluent is selected from water, normal saline, 5% dextrose solution, Lactated Ringer's solution, and combinations thereof.

In at least one embodiment of the present invention, the process further comprises the step of adding a bulking agent selected from mannitol, lactose, sucrose, sodium chloride, trehalose, dextrose, starch, hydroxyethylstarch (hetastarch), cellulose, cyclodextrins, glycine, and combinations thereof.

The present invention also relates to a pharmaceutical formulation prepared by a process comprising the steps of: (a) dissolving at least one excipient and at least one buffer into an aqueous diluent to form an acidic solution, wherein the temperature of the aqueous diluent is in the range of 16 to 24° C. before addition of the excipient and buffer; (b) dissolving a stabilizer either into the solution of step (a) or into the aqueous diluent of step (b) before addition of the excipient and buffer; and (c) dissolving an antineoplastic compound having a cyclic or non-cyclic hydrazine, triazine, or tetrazine group, or a pharmaceutically acceptable salt thereof, into the solution of step (b) at a temperature in the range of 16 to 24° C.; wherein the stabilizer is an antioxidant and/or more susceptible to nucleophilic attack than the antineoplastic compound.

The present invention also relates to a pharmaceutical formulation comprising: an antineoplastic compound having a cyclic or non-cyclic hydrazine, triazine, or tetrazine group, or a pharmaceutically acceptable salt thereof; and a stabilizer, wherein the stabilizer is an antioxidant and/or more susceptible to nucleophilic attack than the antineoplastic compound.

In at least one embodiment of the present invention, the pharmaceutical formulation is a lyophilized powder. Preferably, the lyophilized powder contains less than 0.6 wt % of total impurities, based on the total weight of the lyophilized powder, after storage for 3 months at 40° C./75% RH. Preferably, the lyophilized powder contains less than or equal to 10% of the initial amount of stabilizer added to the formulation.

The present invention also relates to a method for treating a cancer-related disease, comprising parenterally administering a therapeutically effective amount of a pharmaceutical formulation of the present invention to a subject in need thereof. In at least one embodiment of the present invention, the pharmaceutical formulation is a lyophilized powder that is reconstituted prior to administration.

BRIEF DESCRIPTION OF THE DRAWINGS

FIG. 1 is a graph showing stability data for a bulk solution of the present invention held at different temperatures.

DETAILED DESCRIPTION

The present invention relates to pharmaceutical formulations comprising compounds having a cyclic or non-cyclic hydrazine, triazine, or tetrazine group, or a pharmaceutically acceptable salt thereof, that are known to have antineoplastic properties. The main degradation reactions for compounds included in the formulations of the present invention are oxidation and nucleophilic substitution. Regarding nucleophilic substitution, any molecule or ion with a free pair of electrons or at least one pi bond can act as a nucleophile. Hence, aqueous diluents such as water can cause a nucleophilic substitution, resulting in drug degradation and the production of unwanted compounds. For example, nucleophilic substitution will hydrolyze temozolomide to MTIC and will hydrolyze mitozolomide (chemical name: 8-carbamoyl-3-(2-chloroethyl)imidazo[5,1-d]-1,2,3,5-tetrazin-4-(3H)-one) to 5-[3-(2-chloroethyl)triazen 1-yl]-imidazole-4-carboxamide (MCTIC).

Pharmaceutical formulations of the present invention, however, are prepared by a process that protects the active ingredient from oxidation and/or nucleophilic substitution by use of a stabilizer during preparation of the pre-lyophilized bulk solution. Antineoplastic compounds having a cyclic or non-cyclic hydrazine, triazine, or tetrazine group, or a pharmaceutically acceptable salt thereof, that are suitable for use in the present invention include, but are not limited to, altretamine, dacarbazine, mitozolomide, procarbazine, temozolomide, compounds described in U.S. Pat. No. 5,260,291 as having antineoplastic activity (including those of Formula I below), and other antineoplastic alkylating agents having this structural feature. Preferably, the antineoplastic compound is temozolomide.

Formula I

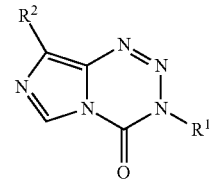

In Formula I, $R^1$ represents hydrogen, or an alkyl, alkenyl or alkynyl group containing from 1 to 6 carbon atoms, or a said group substituted by from one to three substituents selected from halogen atoms, alkoxy, alkylthio, alkylsulphinyl and alkylsulphonyl groups containing up to 4 carbon atoms, and phenyl substituted by alkoxy and alkyl groups containing from 1 to 4 carbon atoms or a nitro group; or $R^1$ represents a cycloalkyl group containing from 3 to 8 carbon atoms, and $R^2$ represents a carbamoyl group, or a carbamoyl group carrying on the nitrogen atom one or two groups selected from alkyl and alkenyl groups containing up to 4 carbon atoms, and cycloalkyl groups containing from 3 to 8 carbon atoms, and, when $R^1$ represents hydrogen, alkali metal salts thereof.

Pharmaceutically acceptable salts of antineoplastic compounds having a cyclic or non-cyclic hydrazine, triazine, or tetrazine group include, but are not limited to, salts prepared from acids such as hydrochloric, hydrobromic, phosphoric, sulfuric, maleic, citric, acetic, tartaric, succinic, oxalic, malic, glutamic, pamoic and the like. Further non-limiting examples of pharmaceutically acceptable inorganic and organic acid addition salts include those listed in S. M. Berge et al., *J. Pharm. Sci.*, 66, 1:2 (1977), and G. S. Paulekuhn, et al., *J. Med. Chem.*, 50, 26:6665-72 (2007).

Temozolomide, a tetrazine derivative known for its antitumor properties, is representative of antineoplastic compounds having a cyclic or non-cyclic hydrazine, triazine, or tetrazine group, or a pharmaceutically acceptable salt thereof. Thus, although this compound is discussed in detail herein, the present invention is not limited to the use of this compound only.

Stabilizers of the present invention have antioxidant properties and/or greater susceptibility to nucleophilic attack than the active compound, thereby protecting the active compound from degradation. That is, suitable stabilizers are capable of protecting the active compound from oxidative degradation, hydrolytic degradation, or both. Stabilizers of the present invention may also include inorganic compounds, that can be consumed during the process such that the lyophilized product is substantially free of stabilizer. As used herein, "substantially free" of stabilizer means that the amount of stabilizer in the lyophilized product is less than or equal to 10% of the initial amount of stabilizer added during preparation of the formulation. Likewise, a stabilizer that is "substantially consumed" during the process of preparing a pharmaceutical formulation of the present invention refers to a stabilizer that is present in the final product (e.g., the lyophilized powder) in an amount that is less than or equal to 10% of the initial amount of stabilizer added during preparation of the formulation (e.g., originally added to the bulk solution). Less than 10% includes amounts that are less than or equal to 5%, less than or equal to 3%, less than or equal to 2%, less than or equal to 1%, less than or equal to 0.5%, as well as trace and undetectable amounts. Thus, for example, if 1.0 mg of stabilizer were added during preparation of a bulk solution of the present invention, the lyophilized powder would be "substantially free of stabilizer" (and the stabilizer would be "substantially consumed") if the lyophilized powder contains less than or equal to 0.1 mg (i.e., 10% of the original 1.0 mg), the rest of the original amount of stabilizer having been consumed during preparation of the bulk solution and lyophilization processing.

Stabilizers that are suitable for use in the present invention include, but are not limited to, alpha tocopherol, ascorbic acid, ascorbyl palmitate, butylated hydroxyanisole, butylated hydroxytoluene, hypophosphorus acid, monothioglycerol, potassium metabisulfite, propionic acid, propyl gallate, sodium ascorbate, sodium bisulfite, sodium formaldehyde sulfoxylate, sodium metabisulfite, sodium sulfite, tartaric acid, and combinations thereof. Other suitable stabilizers are described in Nema et al., "Excipients and Their Use in Injectable Products," *PDA Pharm Sci Tech,* 51:166-170 (1997). Preferably, the stabilizer is inorganic and effective when used in an acidic preparation.

For example, ascorbic and tartaric acids are suitable stabilizers, largely because they possesses antioxidant properties and can thus prevent oxidative degradation of a compound having a cyclic or non-cyclic hydrazine, triazine, or tetrazine group, or a pharmaceutically acceptable salt thereof.

Sodium metabisulfite is another suitable stabilizer because, for example, it is a well-known antioxidant and is more susceptible to nucleophilic attack than a compound having a cyclic or non-cyclic hydrazine, triazine, or tetrazine group, or a pharmaceutically acceptable salt thereof, thus preventing both oxidative and hydrolytic degradation of the active compound Sodium metabisulfite is also an inorganic compound that is substantially consumed during the process of the present invention because, in aqueous media, sodium metabisulfite immediately converts to sodium ($Na^+$) and bisulfite ($HSO_3^-$) ions, which further convert to $SO_2$ gas.

Although sodium metabisulfite is discussed in detail herein, the present invention is not limited to the use of only this stabilizer and equally includes other stabilizers that meet the criteria of having antioxidant properties and/or being more susceptible to nucleophilic attack than a compound having a cyclic or non-cyclic hydrazine, triazine, or tetrazine group. In other words, sodium metabisulfite is representative of stabilizers that are suitable for use in the present invention. Further, the data and results from tests conducted on pharmaceutical formulations containing sodium metabisulfite (discussed herein) are predictive of the results that would be expected if other stabilizers that meet the foregoing criteria were tested.

The following discussion further illustrates the manner in which stabilizers of the present invention can protect compounds having a cyclic or non-cyclic hydrazine, triazine, or tetrazine group by being more susceptible to nucleophilic attack than the active compound. For example, compounds having a cyclic tetrazine group include temozolomide and mitozolomide, the structures of which are shown below.

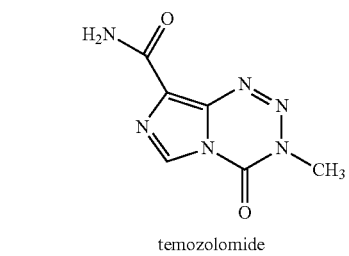
temozolomide

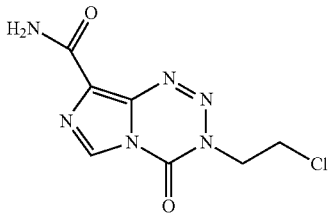
mitozolomide

Nucleophilic attack of temozolomide and mitozolomide and similar compounds (including but not limited to other compounds having a tetrazine group) could occur according to the following reaction scheme, converting the active compound into a degradation product:

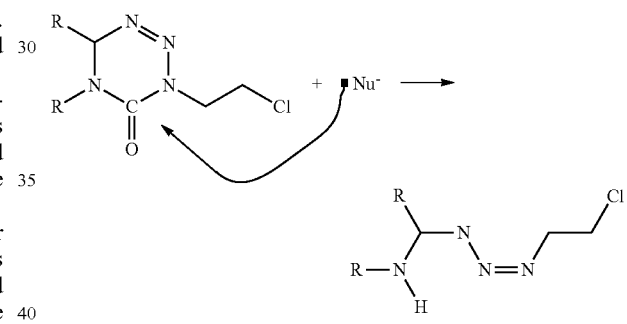

Other suitable compounds having a cyclic or non-cyclic hydrazine, triazine, or tetrazine group include dacarbazine and procarbazine, the structures of which are shown below.

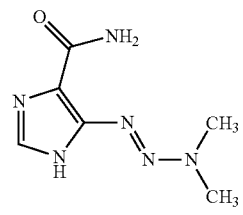
dacarbazine

procarbazine

Nucleophilic attack of dacarbazine and procarbazine and similar compounds (including but not limited to other compounds having a triazine or hydrazine group) could occur according to the following reaction scheme, converting the active compound into a degradation product:

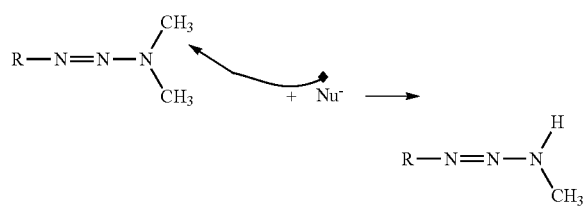

A suitable stabilizer of the present invention that is more susceptible to nucleophilic attack than a compound having a cyclic or non-cyclic hydrazine, triazine, or tetrazine group is sodium metabisulfite, the structure of which is shown below.

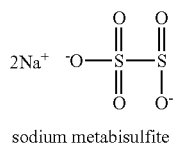

sodium metabisulfite

Nucleophilic attack of sodium metabisulfite and similar compounds (including but not limited to other sulfites, such as potassium metabisulfite, sodium bisulfite, and sodium sulfite), could occur according to the following reaction scheme, thus protecting the active compound from being subjected to nucleophilic attack:

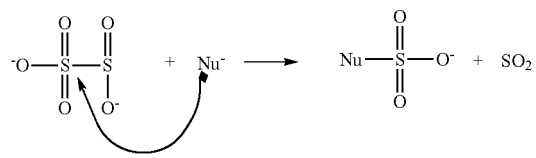

In the present invention, the stabilizer prevents or slows the generation of impurities. As used herein, the term "impurities" refers to unwanted compounds that were not added as reagents during preparation of a pharmaceutical formulation of the present invention. For example, impurities may include products resulting from oxidative or hydrolytic degradation of the active compound, or other degradation products.

As used herein, "diluent" means an aqueous fluid suitable for injection into a patient. Diluents that are suitable for use in the present invention include, but are not limited to, water, normal saline, 5% dextrose solution, Lactated Ringer's solution, and other fluids suitable for injection into a patient, preferably suitable for intravenous injection, including infusion, into a patient.

Pharmaceutical formulations of the present invention may contain one or more excipient, such as polysorbate, polyethylene glycol, propylene glycol, polypropylene glycol, and combinations thereof. Additional components, such as buffers and bulking agents may also be included.

As used herein, "buffers" refers to pH-adjusting agents that are acidic in nature. Buffers that are suitable for use in the present invention include, but are not limited to, lithium citrate monohydrate, sodium citrate monohydrate, potassium citrate monohydrate, calcium citrate monohydrate, lithium citrate dihydrate, sodium citrate dihydrate, potassium citrate dihydrate, calcium citrate dihydrate, lithium citrate trihydrate, sodium citrate trihydrate, potassium citrate trihydrate, calcium citrate trihydrate, lithium citrate tetrahydrate, sodium citrate tetrahydrate, potassium citrate tetrahydrate, calcium citrate tetrahydrate, lithium citrate pentahydrate, sodium citrate pentahydrate, potassium citrate pentahydrate, calcium citrate pentahydrate, lithium citrate hexahydrate, sodium citrate hexahydrate, potassium citrate hexahydrate, calcium citrate hexahydrate, lithium citrate heptahydrate, sodium citrate heptahydrate, potassium citrate heptahydrate, calcium citrate heptahydrate, lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartarate, sodium tartarate, potassium tartarate, calcium tartarate, lithium succinate, sodium succinate, potassium succinate, calcium succinate, lithium acetate, sodium acetate, potassium acetate, calcium acetate, acetic acid, hydrochloric acid, lactic acid, phthalic acid, and combinations thereof, and other pH-adjusting agents that are acidic in nature.

Bulking agents that are suitable for use in the present invention include, but are not limited to, mannitol, lactose, sucrose, sodium chloride, trehalose, dextrose, starch, hydroxyethylstarch (hetastarch), cellulose, cyclodextrins, glycine, and combinations thereof.

Solubility Study

Temozolomide is only slightly soluble in water (~3.1 mg/ml). The USP defines "slightly soluble" as having a solubility range of 1-10 mg/ml. Although it was thought that temozolomide must be formulated with a dissolution enhancer (e.g., L-threonine in TEMODAR®), the present inventors found that temozolomide has an intrinsic solubility such that a dissolution enhancing agent is not needed in the formulation.

The present inventors assessed the aqueous solubility of temozolomide at pH 1.2, 2.0, 3.0, and 4.5 using the shake-flask method. The results of this study are shown in Table 1. "Final pH" refers to the pH of the aqueous media after addition of temozolomide.

TABLE 1

| Solvent Media | Final pH | Solubility (mg/ml) |
| --- | --- | --- |
| HCl Buffer, USP, pH 1.2 | 1.4 | 7.3 |
| HCl Buffer, USP, pH 2.0 | 2.1 | 7.3 |
| Acid Phthalate Buffer, USP, pH 3.0 | 3.2 | 8.2 |
| Acetate Buffer, USP, pH 4.5 | 4.7 | 7.3 |

The results of this solubility study show that temozolomide has an intrinsic solubility of more than 7 mg/ml that renders it unnecessary to include any solubilizers or dissolution enhancers in the formulation. Further, it was surprisingly shown that changes in pH do not affect the intrinsic solubility of such compounds.

Stability Study—Effect of pH

Temozolomide is only stable in acidic conditions of pH less than 5, and is labile at pH more than 7. Thus, acidic media is needed in order to maintain the stability of a solution containing this compound. Similarly, it is noted that dacarbazine is administered after reconstitution at pH 3-4, and altretamine is increasingly soluble at pH 3 or less. Since acidic media can better maintain the stability of a solution containing an antineoplastic compound having a cyclic or non-cyclic hydrazine, triazine, or tetrazine group, the inventors concluded that adding an acid to the solution should assist in stabilizing the compound. This conclusion was confirmed by stability tests conducted on temozolomide solutions containing various acidic buffers. For each test, the amount of temozolomide was measured as a percentage of the amount originally added to the bulk solution. The results are shown in Tables 2A and 2B.

TABLE 2A

| Buffer Media | 0.1N HCl pH = 1.1 | Hydrochloride Buffer pH = 2.2 | Acetate Buffer pH = 4.5 |
|---|---|---|---|
| Stability after 1 hr | 101.7% | 99.1% | 99.2% |
| Stability after 3 hr | 101.0% | 99.2% | 99.3% |
| Stability after 5 hr | 100.2% | 98.6% | 98.1% |
| Stability after 6 hr | 99.8% | 99.0% | 98.2% |

TABLE 2B

| Buffer Media | Water | Phosphate Buffer pH = 6.8 | Phosphate Buffer pH = 7.5 |
|---|---|---|---|
| Stability after 5 min | 99.9% | 100.1% | 99.4% |
| Stability after 10 min | 99.6% | 99.8% | 99.0% |
| Stability after 15 min | 98.8% | 99.0% | 97.8% |
| Stability after 30 min | 97.6% | 98.0% | 90.5% |

Stability Study—Effect of Stabilizer

After studying the effect of pH on stability, the inventors further found that addition of acid, such as hydrochloric acid, is not sufficient to stabilize the formulation, and that a significantly better impurity profile can be obtained by including a stabilizer that protects the active compound—i.e., a compound that has antioxidant properties and/or provides a better substrate for nucleophilic attack, and preferably one that is inorganic and consumed during preparation of the formulation.

Stability is a concern for compounds in both the liquid solution and solid states. Thus, a significant advantage of the pharmaceutical formulations of the present invention was identified when the inventors found that the presence of a stabilizer inhibits degradation in the solid state as well as the liquid solution state. This is illustrated by a stability study that was conducted using solid powder mixtures of temozolomide and ascorbic acid. Temozolomide and mixtures of 1:1 temozolomide:ascorbic acid were maintained at 40° C./75% relative humidity (RH) to assess the sensitivity of temozolomide to oxidation and the ability of stabilizers to inhibit oxidative degradation. In the tested formulations, the weight percentages of certain degradation products were measured. The results are shown in Table 3.

TABLE 3

| | Temozolomide 1 month 40° C./75% RH | Temozolomide:ascorbic acid (1:1) 1 month 40° C./75% RH |
|---|---|---|
| Dacarbazine-related compound A | 8.4% | 0.03% |
| Max. Unknown | 0.22% | 0.00% |
| Total impurities | 10.13% | 0.03% |

Preparation of Bulk Solution

Pharmaceutical formulations of the present invention are prepared as a bulk solution, which is subjected to lyophilization to form a lyophilized powder, which can be reconstituted with an aqueous diluent prior to administration to a patient in need of antineoplastic treatment.

The bulk solution contains up to about 8 mg/ml of the antineoplastic compound having a cyclic or non-cyclic hydrazine, triazine, or tetrazine group, and preferably at least 2.5 mg/ml. Various desired concentrations in the range of up to about 8 mg/ml can be prepared. The bulk solution of the present invention has an acidic pH above 2, such as from about 2 to about 5, from about 3 to about 4, from about 3.6 to about 4.0, and about 3.8.

In one embodiment, the bulk solution is prepared using the following process steps:

(1) Add an aqueous diluent to a preparation tank at a controlled temperature in the range of 16-24° C., preferably 18-22° C., and more preferably 19-20° C. The tank may then be purged with an inert gas (e.g., $N_2$).

(2) Add and dissolve excipients into the aqueous diluent.

(3) Add and dissolve 0.01 to 1% w/v stabilizer either into the mixture of step (2), or into the aqueous diluent of step (1) before the excipients are added in step (2). Preferably, the stabilizer is added in an amount of 0.05 to 0.5% w/v, more preferably 0.1% w/v.

(4) Add and dissolve an antineoplastic compound having a cyclic or non-cyclic hydrazine, triazine, or tetrazine group into the mixture of step (3); and mix at a controlled temperature in the range of 16-24° C., preferably 18-22° C., and more preferably 19-20° C. until dissolution is complete. The antineoplastic compound may be added in an amount of 0.1 to 0.8% w/v, preferably 0.1 to 0.25% w/v.

The final volume of the bulk solution may be adjusted by adding an aqueous diluent. The resulting solution may then be sterile filtered, preferably using a 0.2 μm filter.

In another embodiment, the bulk solution is prepared using the following process steps:

(1) Add water to a preparation tank at a controlled temperature in the range of 16-24° C., preferably 18-22° C., and more preferably 19-20° C.

(2) Add and dissolve polysorbate, mannitol, sodium citrate dihydrate, and hydrochloric acid into the water.

(3) Add and dissolve 0.01 to 1% w/v sodium metabisulfite either into the mixture of step (2), or into the water of step (1) before the excipients are added in step (2). Preferably, the sodium metabisulfite is added in an amount of 0.05 to 0.5% w/v, more preferably 0.1% w/v.

(4) Add and dissolve temozolomide into the mixture of step (3); and mix at a controlled temperature in the range of 16-24° C., preferably 18-22° C., and more preferably 19-20° C. until dissolution is complete. The temozolomide may be added in an amount of 0.1 to 1.5% w/v, preferably 0.1 to 0.8% w/v, more preferably 0.1 to 0.25% w/v.

The final volume of the bulk solution may be adjusted by adding water. The resulting solution may then be sterile filtered, preferably using a 0.2 μm filter.

Lyophilization

Bulk solutions prepared by the foregoing processes can be filled into vials using standard techniques, including sterile filtration, and then subsequently lyophilized. Lyophilization, also known as freeze-drying, is a process whereby water is sublimed from a composition after it is frozen. In this process, pharmaceutical and biological agents that are relatively unstable in an aqueous solution over a period of time can be placed into dosage containers in an easily processed liquid state, dried without the use of damaging heat, and stored in a dry state for extended periods. Pharmaceutical formulations of the present invention include those in the form of lyophilized powder. Various lyophilization cycles are suitable for lyophilizing bulk solution of the present invention. For example, one suitable lyophilization cycle would have the following parameters:

| Stage | Time (hr:min) | Temperature (° C.) |
|---|---|---|
| Loading | 00:30 | −50 |
| Freezing | 04:30 | −50 |
| Annealing | 01:30 | −20 |
|  | 06:00 | −20 |
| Freezing | 03:00 | −50 |
|  | 03:00 | −50 |
| Primary Drying | 05:00 | 0 |
|  | 20:00 | 0 |
| Secondary Drying | 03:00 | +15 |
|  | 10:00 | +15 |
|  | 03:00 | +35 |
|  | 10:00 | +35 |

In the foregoing exemplary lyophilization cycle, a pressure of 20-70 mTorr may be applied during the primary and secondary drying steps. It is also noted that annealing is important in order to prevent collapse in the final lyophilized powder.

Lyophilized powders of the present invention have a water content of less than or equal to 2 wt %, and preferably less than or equal to 1 wt %, based on the total weight of the lyophilized powder.

Reconstitution

Lyophilized powders of the present invention are reconstituted with an aqueous diluent such as water, normal saline, 5% dextrose solution, Lactated Ringer's solution, and combinations thereof, prior to administration to a patient. In one embodiment, the lyophilized powder contains 2.5 mg/ml active compound after reconstitution with 41 ml water. Other desired concentrations after reconstitution can be achieved as well.

The stability of the pharmaceutical formulations of the present invention is evident in the form of the reconstituted solution as well as bulk solutions and lyophilized products. This enduring stability was illustrated by studying the total percentage of impurities in a reconstituted solution of the present invention and the total percentage of impurities in a reconstituted solution of Comparative Example 1 at room temperature over time.

Consumption of Stabilizer

When the stabilizer is inorganic, it is partly consumed during preparation of the bulk solution, and further consumed during lyophilization such that the amount of stabilizer in the lyophilized product is less than or equal to 10%, preferably less than or equal to 5%, of the initial amount of stabilizer added during preparation of the formulation.

Consumption of sodium metabisulfite is representative of this feature of the present invention. When sodium metabisulfite is included in formulations of the present invention, it slowly oxidizes to sodium sulfate with disintegration of the crystals upon exposure to air and moisture. Further, the addition of strong acids to the solid liberates sulfur dioxide. In water, sodium metabisulfite is immediately converted to sodium ($Na^+$) and bisulfite ($HSO_3^-$) ions that are further converted to $SO_2$ gas.

Consumption of the stabilizer was demonstrated using a lyophilized product prepared by the following process steps: add water to a preparation tank at a controlled temperature in the range of 16-24° C.; add and dissolve polysorbate, mannitol, sodium citrate dihydrate, and hydrochloric acid into the water; add and dissolve sodium metabisulfite; add and dissolve temozolomide while mixing at a controlled temperature in the range of 16-24° C. until dissolution is complete; adjust the final volume of the bulk solution by adding water; sterile filter the solution; and lyophilize to form a powder. The lyophilized powder was initially assayed to measure its sodium metabisulfite content, and was also subsequently assayed to measure the content of sodium metabisulfite under storage conditions at 40° C. and 75% RH. These measured amounts reflect percentages of the amount sodium metabisulfite originally added to the bulk solution during preparation of the tested formulation. The results are shown in Table 4.

TABLE 4

| Test | Initial | 1 month (40° C./75% RH) | 2 months (40° C./75% RH) | 3 months (40° C./75% RH) |
|---|---|---|---|---|
| Assay of sodium metabisulfite (% of initial amount added to bulk solution) | Less than 1% | Less than 1% | Less than 1% | Less than 1% |

Since the "initial" amount of sodium metabisulfite was determined to be less than 1% of the amount of sodium metabisulfite originally added to the bulk solution, it can be concluded that the sodium metabisulfite was substantially consumed during preparation of the lyophilized product—i.e., during preparation of the bulk solution and particularly during lyophilization.

It was also determined that the sodium metabisulfite protected the temozolomide from oxidation and hydrolysis during both preparation and storage.

Effect of Controlled Preparation Temperature

The pharmaceutical formulations of the present invention are prepared at a controlled temperature of 16-24° C., preferably 18-22° C., and more preferably 19-20° C., to facilitate dissolution of the active compound and improve degradation control. This was confirmed by the inventors in forced degradation studies conducted on temozolomide in the dry state. The effect of temperature degradation is expected to be higher in the solution state, when temozolomide is much less stable. A study was conducted in order to evaluate the effect of preparation temperature on the solubility and stability of temozolomide in the final composition. The goal of the study was to determine the minimum temperature at which the active compound could be dissolved within a reasonable time, without affecting the stability of the active ingredient. The results of this study are shown in Table 8.

TABLE 8

| Prep Temp (° C.) | Time (hrs) | Observation |
|---|---|---|
| 10 | About 3 | Temozolomide did not dissolve |
| 15 | About 2 | Temozolomide did not dissolve |
| 18 | About 0.5 to 0.75 | Temozolomide dissolved |
| 19 | About 0.5 to 0.75 | Temozolomide dissolved |
| 20 | About 0.5 to 0.75 | Temozolomide dissolved |
| 24 | About 0.5 to 0.75 | Temozolomide dissolved |
| 25 | About 0.5 to 0.75 | Temozolomide dissolved |

In the studied formulations, an acidic vehicle was selected because temozolomide is stable only at acidic pH values. Specifically, these formulations used water for injection that was acidified before adding temozolomide. It was also shown during the forced degradation studies that the degradation of temozolomide is observed in base hydrolysis and during oxidation. From this, it was understood that a stabilizer, preferably one with antioxidant properties, would be required in order to hold and stabilize a bulk solution of temozolomide until lyophilization.

It was further determined that the acidity of the bulk solution must be optimized in order to yield the best results. As discussed below regarding the Effect of pH on Stability, a bulk solution of the present invention prepared at pH 2.0 contained more impurities after storage for three months at 40° C./75% RH than a bulk solution of the present invention prepared at pH 3.0, and both of the foregoing bulk solutions contained more impurities than a bulk solution of the present invention prepared at pH 3.8.

The above-mentioned controlled preparation temperatures help to dissolve the active compound without the need for added dissolution enhancing agents. These controlled temperatures can also help slow degradation that occurs before lyophilization. Additionally, controlled preparation temperatures reduce degradation and production of impurities during storage. This was confirmed in a study in which a batch of bulk solution prepared according to Example 4 was held at different temperatures. Specifically, one portion of the batch solution was held at 19° C., and another portion was held at 25° C. The results are shown in FIG. 1, which shows that controlled preparation temperature plays a critical role in the stability of compounds having a cyclic or non-cyclic hydrazine, triazine, or tetrazine group. From this, it was determined that the above-mentioned controlled preparation temperatures would significantly help to stabilize pharmaceutical formulations of the present invention.

These temperature control ranges are suitable in pharmaceutical industry. Further, controlled temperatures would also provide better flexibility in production, allowing the bulk solution to be held for some time before lyophilization starts. Those of ordinary skill in the industry know that having more time when the bulk solution can be held is very critical in pharmaceutical manufacturing. Accordingly, the present invention provides a significant advantage over other formulations because, by controlling the process temperature, the formulations of the present invention can remain stable without the need for cold chain control of the finished product.

Another significant advantage of using the controlled preparation temperatures of the present invention is that the lyophilized product does not need to be refrigerated. Unlike TEMODAR®, which must be stored at 2-8° C. until reconstitution, the lyophilized powder prepared according to the present invention is stable at 40° C./75% RH and with a better impurity profile than that of TEMODAR®. In other words, the present invention provides pharmaceutical formulations of lyophilized powder that may be stored with superior stability at temperatures up to 40° C., including room temperature and controlled room temperatures of 20-25° C.

Methods of Treatment

The present invention also relates to methods of treating cancer-related diseases by administering a therapeutically effective amount of a pharmaceutical formulation of the present invention to a subject in need thereof. Such diseases include, but are not limited to, carcinoma, sarcoma, melanoma, glioma, glioblastoma, brain cancer, lung cancer, thyroid follicular cancer, pancreatic cancer, breast cancer, anaplastic astrocytoma, bladder cancer, myelodysplasia, prostate cancer, testicular cancer, colon and rectal cancer, lymphoma, leukemia, and mycosis fungoides.

Pharmaceutical formulations of the present invention are suitable for parenteral administration. As used herein, "parenteral" means subcutaneous, intravenous, intramuscular, intra-articular, intra-synovial, intrasternal, intrathecal, intrahepatic, intralesional, and intracranial injection or infusion techniques. Preferably, the compositions are administered intravenously, more preferably by intravenous infusion.

As used herein, "therapeutically effective amount" means the amount of active ingredient that, when administered to a subject for treating a disease or condition, is sufficient to effect such treatment. This amount will vary depending on the active ingredient, the disease and its severity, and the age, weight, physical condition and responsiveness of the subject to be treated.

As used herein, "subject in need thereof" means an individual, such as a human or other mammal that would benefit from the administration of a pharmaceutical formulation of the present invention.

EXAMPLES

The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Example 1

A pharmaceutical formulation of the present invention containing an antineoplastic compound (temozolomide) and a stabilizer (sodium metabisulfite) was prepared as a bulk solution and lyophilized to form a powder according to the following process steps: add water to a preparation tank at a controlled temperature in the range of 16-24° C.; add and dissolve sodium metabisulfite; add and dissolve polysorbate, mannitol, sodium citrate dihydrate, and hydrochloric acid; adjust pH to 3.6 to 4.0; add and dissolve temozolomide while mixing at a controlled temperature in the range of 16-24° C. until dissolution is complete; adjust the final volume of the bulk solution by adding water; sterile filter the solution; and lyophilize to form a powder. The compositions of the bulk solution and lyophilized powder are shown in the table below.

| Ingredients | mg/ml (bulk solution) | mg/vial* (lyophilized powder) |
|---|---|---|
| Temozolomide | 2.5 | 100 |
| Mannitol USP | 15 | 600 |
| Sodium metabisulfite NF | 1 | 40 |
| HCl (37%) NF | 4 | 160 |
| Polysorbate 80 (Tween 80HP) NF | 3 | 120 |
| Sodium citrate dihydrate USP | 5.875 | 235 |
| Water for Injection | q.s to 1 mL | q.s. to 40 mL |

*Amounts listed for the lyophilized powder are theoretical, not measured. The actual amount of sodium metabisulfite in the lyophilized powder is expected to be less than 10% of the amount originally added to the bulk solution. See, e.g., Consumption of Stabilizer (above) and Example 5 (below).

Example 2

A pharmaceutical formulation of the present invention containing an antineoplastic compound (temozolomide) and a stabilizer (sodium metabisulfite) was prepared as a bulk solution and lyophilized to form a powder using the same process as Example 1. The compositions of the bulk solution and lyophilized powder are shown in the table below.

| Ingredients | mg/ml (bulk solution) | mg/vial* (lyophilized powder) |
| --- | --- | --- |
| Temozolomide | 2.5 | 100 |
| Mannitol USP | 15 | 600 |
| Sodium metabisulfite NF | 1 | 40 |
| HCl (37%) NF | 6 | 240 |
| Polysorbate 80 (Tween 80HP) NF | 3 | 120 |
| Sodium citrate dihydrate USP | 5.875 | 235 |
| Water for Injection | q.s to 1 mL | q.s. to 40 mL |

*Amounts listed for the lyophilized powder are theoretical, not measured. The actual amount of sodium metabisulfite in the lyophilized powder is expected to be less than 10% of the amount originally added to the bulk solution. See, e.g., Consumption of Stabilizer (above) and Example 5 (below).

Example 3

A pharmaceutical formulation of the present invention containing an antineoplastic compound (temozolomide) and a stabilizer (sodium metabisulfite) was prepared as a bulk solution and lyophilized to form a powder using the same process as Example 1. The compositions of the bulk solution and lyophilized powder are shown in the table below.

| Ingredients | mg/ml (bulk solution) | mg/vial* (lyophilized powder) |
| --- | --- | --- |
| Temozolomide | 2.5 | 100 |
| Mannitol USP | 15 | 600 |
| Sodium metabisulfite NF | 1 | 40 |
| HCl (37%) NF | 8 | 320 |
| Polysorbate 80 (Tween 80HP) NF | 3 | 120 |
| Sodium citrate dihydrate USP | 5.875 | 235 |
| Water for Injection | q.s to 1 mL | q.s. to 40 mL |

*Amounts listed for the lyophilized powder are theoretical, not measured. The actual amount of sodium metabisulfite in the lyophilized powder is expected to be less than 10% of the amount originally added to the bulk solution. See, e.g., Consumption of Stabilizer (above) and Example 5 (below).

Example 4

A pharmaceutical formulation of the present invention containing an antineoplastic compound (temozolomide) and a stabilizer (sodium metabisulfite) was prepared as a bulk solution and lyophilized to form a powder according to the following process steps: add water to a preparation tank at a controlled temperature in the range of 16-24° C.; add and dissolve polysorbate, mannitol, sodium citrate dihydrate, and hydrochloric acid; add and dissolve sodium metabisulfite; adjust pH to 3.6 to 4.0; add and dissolve temozolomide while mixing and separate into two portions—one mixed at a controlled temperature of 19° C., and the other mixed at a controlled temperature of 25° C.—until dissolution is complete; adjust the final volume of each bulk solution portion by adding water; sterile filter each solution; and subsequently lyophilize each to form a powder. The compositions of the bulk solutions and lyophilized powders are shown in the table below.

| Ingredients | mg/ml (bulk solution) | mg/vial* (lyophilized powder) |
| --- | --- | --- |
| Temozolomide | 2.5 | 100 |
| Mannitol USP | 15 | 600 |
| Sodium metabisulfite NF | 1 | 40 |
| HCl (37%) NF | 4 | 160 |
| Polysorbate 80 (Tween 80HP) NF | 3 | 120 |
| Sodium citrate dihydrate USP | 5.875 | 235 |
| Water for Injection | q.s to 1 mL | q.s. to 40 mL |

*Amounts listed for the lyophilized powder are theoretical, not measured. The actual amount of sodium metabisulfite in the lyophilized powder is expected to be less than 10% of the amount originally added to the bulk solution. See, e.g., Consumption of Stabilizer (above) and Example 5 (below).

Example 5

A pharmaceutical formulation of the present invention containing an antineoplastic compound (temozolomide) and a stabilizer (sodium metabisulfite) was prepared as a bulk solution and lyophilized to form a powder using the same process as Example 4. The compositions of the bulk solution and lyophilized powder are shown in the table below.

| Ingredients | mg/ml (bulk solution) | mg/vial (lyophilized powder) |
| --- | --- | --- |
| Temozolomide | 2.5 | 100 |
| Mannitol USP | 15 | 600 |
| Sodium metabisulfite NF | 5.875 | 235 |
| HCl (37%) NF | 4 | 160 |
| Polysorbate 80 (Tween 80HP) NF | 3 | 120 |
| Sodium citrate dihydrate USP | 1 | 40 |
| Water for Injection | q.s to 1 ml | q.s to 40 ml |

The lyophilized powder of Example 5 is substantially free of the stabilizer (sodium metabisulfite) because the lyophilized powder contains only 2.5% of the amount of stabilizer originally added to the bulk solution (i.e., 5.875 mg is 2.5% of the original 235 mg).

Comparative Example 1

In this example, a bulk solution and lyophilized powder of a formulation that contains an antineoplastic compound (temozolomide) and a dissolution enhancer (L-threonine) was assessed. The bulk solution and lyophilized powder were prepared according to the following process steps: add water to a preparation tank; add and dissolve L-threonine; add and dissolve polysorbate, mannitol, sodium citrate dihydrate, and hydrochloric acid; adjust pH to 3.6 to 4.0; add and dissolve temozolomide while mixing at a controlled temperature in the range of 16-24° C. until dissolution is complete; adjust the final volume of the bulk solution by adding water; sterile filter the solution; and lyophilize to form a powder. The compositions of the bulk solution and lyophilized powder are shown in the table below.

| Ingredients | mg/ml (bulk solution) | mg/vial (lyophilized powder) |
| --- | --- | --- |
| Temozolomide | 2.5 | 100 |
| Mannitol USP | 15 | 600 |
| L-Threonine | 4 | 160 |
| HCl (37%) NF | 4 | 160 |
| Polysorbate 80 (Tween 80HP) NF | 3 | 120 |
| Sodium citrate dihydrate USP | 5.875 | 235 |
| Water for Injection | q.s to 1 mL | q.s. to 40 mL |

Comparative Example 2

A formulation containing an antineoplastic compound (temozolomide) without a stabilizer and without the dissolution enhancer L-threonine was prepared as a bulk solution and lyophilized to form a powder according to the following process steps: add water to a preparation tank at a controlled temperature in the range of 16-24° C.; add and dissolve polysorbate, mannitol, sodium citrate dihydrate, and hydrochloric acid; adjust pH to 3.6 to 4.0; add and dissolve temozolomide while mixing at a controlled temperature in the range of 16-24° C. until dissolution is complete; adjust the final volume of the bulk solution by adding water; sterile filter the solution; and lyophilize to form a powder. The compositions of the bulk solution and lyophilized powder are shown in the table below.

| Ingredients | mg/ml (bulk solution) | mg/vial (lyophilized powder) |
|---|---|---|
| Temozolomide | 2.5 | 100 |
| Mannitol USP | 15 | 600 |
| HCl (37%) NF | 4 | 160 |
| Polysorbate 80 (Tween 80HP) NF | 3 | 120 |
| Sodium citrate dihydrate USP | 5.875 | 235 |
| Water for Injection | q.s to 1 mL | q.s. to 40 mL |

Effect of L-Threonine on Solubility

L-threonine is a dissolution enhancing agent used in some temozolomide formulations. See, e.g., U.S. Pat. No. 6,987,108. The present inventors conducted a study to determine whether the presence of L-threonine has a significant effect on solubility. In this study, different batches were prepared using temozolomide with and without L-threonine at controlled temperature. The time for temozolomide to go into solution during preparation of the bulk solution ("time for complete dissolution) was measured for each batch. The amount of temozolomide was also measured as a percentage of the amount originally added to the bulk solution. The results are shown in Table 5.

TABLE 5

| Formulation Batch | Temozolomide (%) | Time for complete dissolution (min) | Time for reconstitution of lyophilized powder (sec) |
|---|---|---|---|
| Comparative Example 1 | 101.5 | 30 | 30 |
| Comparative Example 2 | 101.7 | 30 | 30 |
| Comparative Example 2 | 98.1 | 30 | 30 |

The results of this study show that the presence or absence of L-threonine has no effect on temozolomide solubility. The time for complete dissolution was the same for batches prepared with and without L-threonine, and the time for reconstitution of lyophilized powder was also the same for batches prepared with and without L-threonine. Consequently, there is no need for a dissolution enhancing agent in a temozolomide formulation.

Effect of L-Threonine on Stability

Upon comparing the impurity profiles of batches prepared according to Comparative Example 1 and Comparative Example 2, it was found that the impurity profiles for the two approaches (i.e., with L-threonine Comparative Example 1, and without L-threonine in Comparative Example 2) are completely different during storage, especially with respect to unknown impurities and dacarbazine-related compound A. Specifically, higher levels of impurities were measured in the batch prepared without L-threonine as compared to the batch prepared with L-threonine. The results of this comparison are shown in Table 6.

TABLE 6

| | Batch of Comp Ex 1 (with L-threonine) (wt %) | | Batch of Comp Ex 2 (without L-threonine) (wt %) | |
|---|---|---|---|---|
| Impurity Profile | Initial | 3 M @ 40° C./ 75% RH | Initial | 3 M @ 40° C./ 75% RH |
| Dacarbazine-related compound A | 0.245 | 0.395 | 0.225 | 0.329 |
| 2-oxohypoxanthine | 0.013 | 0.071 | 0.008 | 0.000 |
| Maximum unknown | 0.019 | 0.104 | 0.019 | 0.301 |
| Total impurities | 0.281 | 0.625 | 0.254 | 0.909 |

Given the foregoing, it can be concluded that the presence of L-threonine is related to the inhibition of temozolomide degradation rather enhanced dissolution of temozolomide. Accelerated stability studies conducted on batches of Comparative Example 1 and Comparative Example 2 further showed that the degradation of temozolomide is observed during hydrolysis and oxidation.

Effect of Stabilizer on Stability

In order to further assess the effect of a stabilizer on impurity profiles, trials were conducted using a formulation prepared according to Example 1. The impurity profile of this formulation was compared with the impurity profile of a formulation prepared according to Comparative Example 1. When a stabilizer was included in the formulation, the resulting impurity profile was found to be very satisfactory and comparable to the impurity profile of Comparative Example 1. In fact, it was surprisingly found that the 3-month accelerated stability data for the batch of Example 1 was superior to the 3-month accelerated stability data for the batch of Comparative Example 1. The impurity profile of Comparative Example 1 is shown in Table 6. The impurity profile of Example 1 is shown in Table 7.

TABLE 7

| | Batch of Example 1 (with sodium metabisulfite) (wt %) | |
|---|---|---|
| Impurity Profile | Initial | 3 M @ 40° C./75% RH |
| Dacarbazine-related compound A | 0.062 | 0.14 |
| 2-oxohypoxanthine | 0.00 | 0.033 |
| Maximum unknown | 0.048 | 0.16 |
| Total impurities | 0.154 | 0.37 |

Conclusions: Temozolomide bulk solution prepared with sodium metabisulfite as a stabilizer (and without L-threonine) has fewer impurities than temozolomide bulk solution prepared with L-threonine (and without a stabilizer). Consequently, a temozolomide bulk solution prepared with sodium metabisulfite may be lyophilized and stored at 25° C., unlike TEMODAR® lyophilized powder which must be refrigerated at 2-8° C.

From the foregoing, it can also be concluded that other antineoplastic compounds having a cyclic or non-cyclic hydrazine, triazine, or tetrazine group would have likewise improved impurity profiles if prepared in accordance with the present invention. Consequently, lyophilized powders of the present invention include those that contain less than 0.6 wt %, less than 0.5 wt %, less than 0.4 wt %, or even less than 0.3 wt % of total impurities, based on the total weight of the lyophilized powder, after storage for 3 months at 40° C./75% RH.

Effect of pH on Stability

In order to further study the effect of pH on the stability of compounds having a cyclic or non-cyclic hydrazine, triazine, or tetrazine group, three batches were prepared with temozolomide and sodium metabisulfite, each of which was prepared at a different pH. A comparison of the corresponding impurity profiles for these batches is shown in Table 8.

TABLE 8

| Impurity Profile | Batch of Example 2 (at pH = 3.0) (wt %) | | Batch of Example 3 (at pH = 2.0) (wt %) | | Batch of Example 1 (at pH = 3.8) (wt %) | |
|---|---|---|---|---|---|---|
| | Initial | 3M @ 40° C./75% RH | Initial | 3M @ 40° C./75% RH | Initial | 3M @ 40° C./75% RH |
| Dacarbazine Impurity A | 0.143 | 0.289 | 0.135 | 1.45 | 0.062 | 0.14 |
| Maximum unknown | 0.029 | 0.203 | 0.019 | 0.45 | 0.048 | 0.16 |
| Total Impurities | 0.173 | 0.652 | 0.154 | 2.307 | 0.154 | 0.37 |

The above data shows that the batch prepared at pH 3.0 has a superior impurity profile and thus superior stability as compared to the batch prepared at pH 2.0, and that the batch prepared at pH 3.8 exhibited even greater stability as evidenced by the low amount of total impurities (0.37 wt %) after storage at 40° C./75% RH for three months. In other words, the batches prepared at pH 3.0 and pH 3.8 both exhibited superior impurity profiles and thus superior stability as compared to the batch prepared at a pH of 2.0.

Conclusions: The final pH for the bulk solution of the present invention should be above 2.0, and preferably 3.8, in order to ensure good stability for compounds having a cyclic or non-cyclic hydrazine, triazine, or tetrazine group such as temozolomide. However, since temozolomide is only stable at acidic pH, the acidity of the bulk solution must be optimized in order to yield the best results, being mindful that high acidity may enhance degradation as in the case of bulk solutions prepared at pH 2.0.

Comparison of pH of Bulk Solution and Lyophilized Powder

Batches of bulk solution and subsequent lyophilized powder were prepared according to Example 1, Comparative Example 1, and Comparative Example 2. The pH of each was measured and compared. The results are in shown in Table 9.

TABLE 9

| Formulation Batch | pH of bulk solution | pH of lyophilized powder |
|---|---|---|
| Example 1 | 3.7 | 4.2 |
| Comparative Example 1 | 4.0 | 4.4 |
| Comparative Example 2 | 3.7 | 4.2 |

Effect of Controlled Preparation Temperature on Stability

A batch of lyophilized powder was prepared according to Example 1, and its impurity profile was assessed after storage for three months at 40° C./75% RH. The initial impurity profile of purchased TEMODAR® lyophilized powder (which had been refrigerated at 2-8° C. prior to testing) was assessed as well. The comparative results are shown in Table 10.

TABLE 10

| Impurity Profile | TEMODAR® (Initial) (wt %) | Batch of Example 1 (3M @ 40° C./75% RH) (wt %) |
|---|---|---|
| Dacarbazine-related compound A | 0.40 | 0.14 |
| Maximum unknown | 0.10 | 0.03 |
| Total impurities | 0.63 | 0.37 |

The above stability data shows that the formulation of the present invention has a much better impurity profile than TEMODAR®. Moreover, lyophilized powder prepared according to the present invention can be stored at temperatures up to 40° C., including room temperature and controlled room temperatures of 20-25° C. In contrast, TEMODAR® lyophilized powder must be kept refrigerated at 2-8° C.

All publications, patents, articles, and other references cited and/or discussed in this specification are incorporated herein by reference in their entireties and to the same extent as if each reference was individually incorporated by reference.

We claim:

1. A process for preparing a pharmaceutical formulation, comprising the steps of:
   (a) dissolving at least one excipient and at least one buffer into an aqueous diluent to form an acidic solution, wherein the temperature of the aqueous diluent is in the range of 16 to 24° C. before addition of the excipient and buffer;
   (b) dissolving a stabilizer either into the solution of step (a) or into the aqueous diluent of step (a) before addition of the excipient and buffer;
   (c) dissolving an antineoplastic compound having a cyclic or non-cyclic hydrazine, triazine, or tetrazine group, or a pharmaceutically acceptable salt thereof, into the solution of step (b) at a temperature in the range of 16 to 24° C.; and
   (d) adding a bulking agent selected from mannitol, lactose, sucrose, sodium chloride, trehalose, dextrose, starch, hydroxyethylstarch (hetastarch), cellulose, cyclodextrins, glycine, and combinations thereof;
   wherein the stabilizer is an antioxidant and/or more susceptible to nucleophilic attack than the antineoplastic compound.

2. The process of claim 1, further the comprising the step of lyophilizing the solution of step (c) to yield a lyophilized powder that contains less than 0.6 wt % of total impurities, based on the total weight of the lyophilized powder, after storage for 3 months at 40° C./75% RH.

3. The process of claim 2, wherein the lyophilized powder contains less than 0.4 wt % of total impurities after storage for 3 months at 40° C./75% RH.

4. The process of claim 2, wherein the lyophilized powder contains less than or equal to 10% of the initial amount of stabilizer added in step (b).

5. The process of claim 1, wherein the stabilizer is added in step (b) in an amount of 0.01 to 1% w/v.

6. The process of claim 1, further comprising the step of adjusting the pH of the solution of step (c) to about 3 to about 4.

7. The process of claim 1, wherein the antineoplastic compound is selected from altretamine, dacarbazine, mitozolomide, procarbazine, and temozolomide.

8. The process of claim 7, wherein the antineoplastic compound is temozolomide.

9. The process of claim 1, wherein the stabilizer is an antioxidant.

10. The process of claim 1, wherein the stabilizer is selected from alpha tocopherol, ascorbic acid, ascorbyl palmitate, butylated hydroxyanisole, butylated hydroxytoluene, hypophosphorus acid, monothioglycerol, potassium metabisulfite, propionic acid, propyl gallate, sodium ascorbate, sodium bisulfite, sodium formaldehyde sulfoxylate, sodium metabisulfite, sodium sulfite, tartaric acid, and combinations thereof.

11. The process of claim 10, wherein the stabilizer is sodium metabisulfite.

12. The process of claim 1, wherein the excipient is selected from polysorbate, polyethylene glycol, propylene glycol, polypropylene glycol, and combinations thereof.

13. The process of claim 1, wherein the buffer is selected from sodium citrate dihydrate, hydrochloric acid, and combinations thereof.

14. The process of claim 1, wherein the aqueous diluent is selected from water, normal saline, 5% dextrose solution, Lactated Ringer's solution, and combinations thereof.

\* \* \* \* \*